(12) United States Patent
Kaneblei (10) Patent No.: US 11,668,690 B2
(45) Date of Patent: Jun. 6, 2023

(54) MOBILE MEASURING DEVICE, SYSTEM AND PROCESS FOR A SAFETY-RELEVANT APPLICATION

(71) Applicant: Dräger Safety AG & Co. KGaA, Lübeck (DE)

(72) Inventor: Ingo Kaneblei, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 307 days.

(21) Appl. No.: 16/941,047

(22) Filed: Jul. 28, 2020

(65) Prior Publication Data

US 2021/0033584 A1 Feb. 4, 2021

(30) Foreign Application Priority Data

Jul. 31, 2019 (DE) ...................... 10 2019 005 359.1

(51) Int. Cl.
| | |
|---|---|
| *G01N 33/00* | (2006.01) |
| *H02J 7/00* | (2006.01) |
| *G01P 13/00* | (2006.01) |
| *G01R 21/00* | (2006.01) |

(52) U.S. Cl.
CPC ....... *G01N 33/007* (2013.01); *G01N 33/0073* (2013.01); *G01P 13/00* (2013.01); *G01R 21/00* (2013.01); *H02J 7/0047* (2013.01); *G01N 33/0062* (2013.01)

(58) Field of Classification Search
CPC ............ G01N 33/007; G01N 33/0062; G01N 33/0073; H02J 7/0047; H02J 7/00; H02J 9/005; H02J 7/0029; H02J 7/0031; G01P 13/00; G01R 21/00; G05B 19/04; G01D 21/00

USPC ...... 73/23.2, 23.31, 23.34, 31.01, 31.02, 78, 73/81–84, 865.8; 340/632–634
See application file for complete search history.

(56) References Cited

U.S. PATENT DOCUMENTS

2012/0198932 A1* 8/2012 Van Dijk ............. A61B 5/6822
73/488
2013/0344609 A1 12/2013 Mayer et al.

FOREIGN PATENT DOCUMENTS

| CA | 2999705 | * | 6/2011 |
|---|---|---|---|
| DE | 102014015910 A1 | | 5/2016 |
| DE | 102017209474 A1 | | 12/2018 |
| KR | 101897758 | * | 9/2018 |
| WO | 2018224373 A1 | | 12/2018 |

\* cited by examiner

*Primary Examiner* — Robert R Raevis
(74) *Attorney, Agent, or Firm* — McGlew and Tuttle, P.C.

(57) ABSTRACT

A safety application mobile measuring device (100) includes a control unit (110) and a detection unit (120). The control unit controls changes between a switched-on state and a switched-off state depending on a received detection signal (112). The detection unit monitors, in the switched-off state, whether a switch-on condition (414) is present and outputs the detection signal, which indicates a change into the switched-on state which is to be carried out. The detection unit monitors the switched-on state as to whether at least two switch-off conditions (444, 448) are present and outputs the detection signal, which indicates a change into the switched-off state, which is to be carried out, in the presence of at least two switch-off conditions. At least two detection devices (122, 124) each carry out a detection corresponding to the at least one switch-on condition and to the at least two switch-off conditions.

13 Claims, 4 Drawing Sheets

MOBILE MEASURING DEVICE, SYSTEM AND PROCESS FOR A SAFETY-RELEVANT APPLICATION

CROSS REFERENCE TO RELATED APPLICATIONS

This application claims the benefit of priority under 35 U.S.C. § 119 of German Application 10 2019 005 359.1, filed Jul. 31, 2019, the entire contents of which are incorporated herein by reference.

TECHNICAL FIELD

The present invention pertains to a mobile measuring device for a safety-relevant application as well as to a system for switching at least one mobile measuring device on and off automatically. The present invention further pertains to a process for switching at least one mobile measuring device on and off automatically.

TECHNICAL BACKGROUND

Mobile measuring devices, e.g., mobile gas-measuring devices, require a mobile energy supply unit that can only have a limited energy reserve. It is therefore a known goal in the manufacture and the use of mobile measuring devices to keep the energy consumption during the use as low as possible in order for a long operating time with the smallest possible number of charge cycles to be able to be made possible for the mobile measuring device.

It is generally known against this background that mobile measuring devices should be put into an energy-saving sleep mode if no movement was detected over a predefined time period. Furthermore, it is known that mobile measuring devices can be switched off automatically after they have been placed into a charging station intended for the mobile measuring device.

SUMMARY

An object of the present invention is to provide an improved mobile measuring device for a safety-relevant application, especially a mobile measuring device, which makes possible both a low energy consumption and an especially high level of safety for the user.

To accomplish this object, a mobile measuring device is proposed according to the present invention according to a first aspect of the present invention for a safety-relevant application with a control unit and with a detection unit.

The control unit is configured to control a change between the switched-on state and the switched-off state of the mobile measuring device as a function of a received detection signal.

The detection unit is configured to monitor in the off state whether at least one switch-on condition is present and to output the detection signal in the presence of the at least one switch-on condition, said detection signal indicating a change into the switched-on state, which change is to be carried out. The switch-on condition comprises here detection of a movement of the mobile measuring device, detection of a position of the mobile measuring device, detection of the ending of a charging process of the mobile measuring device and/or detection of a predefined current time.

Furthermore, the detection unit is configured to automatically/automatedly monitor in the switched-on state whether at least two switch-off conditions are present and to output the detection signal in the presence of at least two switch-off conditions, the detection signal indicating a change into the switched-off state, which change is to be carried out. The switch-off conditions comprise detection of a continuous absence of movement, detection of a position of the mobile measuring device, detection of a start of a charging process of the mobile measuring device and/or detection of a predefined current time.

Further, the detection unit comprises at least two detection devices, which are configured to carry out a respective detection corresponding to the at least one switch-on condition and the at least two switch-off conditions.

It was discovered within the framework of the present invention that the provision of two switch-off conditions is advantageous for ensuring a high level of safety for the user, because an accidental switching off of the mobile measuring device is avoided thereby. As a result, it can be reliably ensured that the mobile measuring device will not be switched off accidentally during a use within the framework of the safety-relevant application and the user will not be exposed to an increased risk as a result. In particular, it is avoided by the mobile measuring device according to the present invention with the at least two switch-off conditions that the measuring device will not switch itself off accidentally, for example, because a user put the device down and a sleep mode was activated as a result based on the absence of movement. Furthermore, it was discovered that an automated switching on and switching off of the mobile measuring device reduces the risk of a manual operating error especially reliably.

The provision of at least two detection devices for detecting the switch-on and switch-off conditions reduces the probability that the at least two switch-off conditions are present in an erroneous manner based on an error within only one detection device.

The provision of at least one detectable switch-on condition ensures that the mobile measuring device does not accidentally remain switched off during the safety-relevant application. The mobile measuring device according to the present invention thus makes it possible that switching on takes place in a reliable and automated manner (automatedly) and switching off takes place in a multiply secured manner, i.e., that it does not take place accidentally.

Moreover, the mobile measuring device is an especially energy-saving device due to the automated switching off according to the present invention and it therefore makes possible a long operating time of the mobile measuring device between two charging cycles.

The provision of switch-on and switch-off conditions monitored in an automated manner advantageously reduces the necessary manual interaction between the user and the mobile measuring device. A separate manual control is not ruled out by the present invention.

Furthermore, the operating effort for a user of the mobile measuring device is reduced by the change between switched-on state and switched-off state, which is automated according to the present invention.

Furthermore, provisions may be made according to the present invention for manual operation or at least a manual switching on and off not to be possible, so that a manual operating error becomes entirely impossible.

In case of a manual operating error, the automated monitoring according to the present invention nevertheless ensures an automated switching on and switching off and ensures a high level of safety for the user as a result.

The switched-off state of the mobile measuring device is a state in which the mobile measuring device consumes very little energy compared to the switched-on state. Only the detection devices of the detection unit, which are necessary for monitoring the presence of the at least one switch-on condition, are typically supplied with current in the switched-off state. Furthermore, a potential may continue to be present on a sensor of the mobile measuring device in the switched-off state. As a result, operation of the mobile measuring device can be resumed especially rapidly after switching on.

The detection of a beginning or ending of a charging process of the mobile measuring device means in some embodiments according to the present invention the detection of a connection or removal of a charger for the mobile measuring device.

Preferred embodiments of the mobile measuring device according to the present invention will be described below.

In one embodiment, the presence of a plurality of switch-on conditions and/or of more than two different switch-off conditions is monitored, and the corresponding detection signal is outputted by the detection unit in the presence of a switch-on condition of the plurality of monitored switch-on conditions and/or in the presence of two different switch-off conditions of the more than two different monitored switch-off conditions. The presence of switch-on and/or switch-off conditions is monitored especially reliably by the detection unit in this embodiment.

In a preferred embodiment, the detection unit is configured to monitor whether at least two switch-on conditions are present and to output the corresponding detection signal in the presence of the at least two switch-on conditions. The provision of at least two switch-on conditions supports energy saving by the mobile measuring device between two uses, because the risk of an accidental automated switching on is reduced. In one variant of this embodiment, the at least two switch-on conditions comprise two switch-on conditions from the group of switch-on conditions.

In one embodiment, the detection unit is configured to monitor whether at least three switch-off conditions are present and to output the corresponding detection signal in the presence of the at least three switch-off conditions. An incorrect switching off of the mobile measuring device is avoided especially reliably in this embodiment.

In another preferred embodiment, the mobile measuring device further comprises a user interface, which is configured to receive a manual user input, and wherein the control unit is further configured to control the change between switched-on state and switched-off state depending on the manual user input. In a variant of this embodiment, the user input is a button, an adjusting wheel or a touch sensor. The user of the mobile measuring device can advantageously ensure in this embodiment that the mobile measuring device is switched on with certainty at the beginning of the safety-relevant application, without having to trust that the switch-on condition is present. Further, both the change into the switched-on state and the change into the switched-off state can be controlled in one variant via the user interface. As a result, the switching on and switching off of the mobile measuring device can be controlled basically by the user, and the automated monitoring according to the present invention only acts as a supportive measure in order to avoid an operating error. In another variant of this embodiment, the user interface is only configured to switch on the mobile measuring device. An accidental switching off of the mobile measuring device is avoided especially effectively in this variant, because a manual switching off of the mobile measuring device is not possible at all.

In a preferred embodiment, the detection unit has a detection device for detecting a movement. This detection device preferably comprises an acceleration sensor, a brightness sensor, a vibration sensor, a temperature sensor, a tilt switch and/or an optical sensor. These detection devices are typically favorable and can be manufactured in a simple manner. These detection devices are generally known, so that the particular structure will not be explained in detail below. Detection devices for the detection of a movement are typically very robust, so that an especially reliable monitoring of the switch-on and/or switch-off conditions is possibly by means of such a detection device. A detected movement of the mobile measuring device typically indicates that the mobile measuring device is not currently being stored and could therefore be in use for a safety-relevant application. A detected movement represents in this example a switch-on condition. By contrast, the detection of a continuous absence of movement may indicate the presence of a state of rest for the mobile measuring device and therefore represent a switch-off condition in an example of this embodiment.

In another advantageous embodiment, the detection unit has a detection device for the detection of a position. This detection device preferably comprises a GPS sensor, a wireless module, an optical sensor, a magnetic sensor and/or an induction sensor. The detection devices according to this variant function each independently from an external device, which makes possible detection of the position of the measuring device within the mobile measuring device by an interaction with the detection device. Switching on or switching off of the measuring device can be inferred especially reliably by detection of the position of the measuring device, because the safety-relevant application of the mobile measuring device is typically only necessary within a predefined local area.

In a preferred variant of the above embodiment, the wireless module receives an identification signal and is configured to indicate the change to be carried out between the switched-on state and the switched-off state as a function of a piece of identification information indicated by the received identification signal, especially the presence of a corresponding switch-on or switch-off condition. For example, the identification signal may indicate in this variant by the identification information that the mobile measuring device is located within an area intended for the storage, so that no safety-relevant application is currently taking place. A switch-off condition is present in this case due to the reception of the identification information. In an alternative or additional example of this variant, the identification signal may indicate by the identification information that the mobile measuring device is located in a safety-relevant area for the safety-relevant application. A switch-on condition is present in this case due to the reception of the identification information.

In another advantageous embodiment, the detection unit has a detection device for the detection of a time. This detection device preferably comprises here a timer. The detection unit according to this embodiment is especially advantageous if the safety-relevant application begins at a predefined time and ends at another predefined time. In a variant of this embodiment, switch-off times predefined by the detection unit, at which the safety-relevant application is not present, are stored, so that one of the two switch-off conditions is met with certainty with the detection of this predefined time.

In another advantageous embodiment, the detection unit has a detection device for detecting a beginning or ending of a charging process. This detection device detects a change in an electric power being fed to the mobile measuring device and/or a severing or connection of an electrical or inductive contact via a corresponding connection. The safety-relevant application is not typically present during the charging process, so that the corresponding switch-off condition can be detected in this embodiment with an especially high level of reliability. In an alternative or additional embodiment, the mobile measuring device is charged via a solar module, in which case a lighting unit, which ensures the charging of the mobile measuring device during the storage between two uses, for example, by an LED light, is provided as an external charging station. The detection unit is preferably configured in this embodiment to detect the switching on and/or switching off of the external charging station. If the external charging station is switched on, a switch-off condition is present for the change of the mobile measuring device into the switched-off state, because no safety-relevant application is typically present during a charging process.

In an especially preferred embodiment, the at least two switch-off conditions are monitored by two different detection devices of the detection unit. It is ensured hereby that a defect of one detection device does not lead to an accidental switching off of the mobile measuring device.

In another especially preferred embodiment, the detection unit has at least two detection devices, wherein the at least two detection devices are configured to detect at least two different types of conditions from the following group of types of conditions: Detection of a movement, detection of a position, detection of a beginning or ending of a charging process, and detection of a predefined current time. It is ensured in this embodiment that only two conditions not correlated with one another will lead to the detection of two switch-off conditions. For example, it is ensured in this embodiment that two different detected switch-off conditions pertaining to a movement of the mobile measuring device will not accidentally lead to a switching off of the mobile measuring device during the safety-relevant application.

In an especially preferred embodiment, the mobile measuring device is a mobile gas-measuring device. The circumstance that mobile gas-measuring devices typically have a very low energy consumption is utilized especially advantageously in this embodiment, so that an energy-efficient operation can lead to an especially long operating time of the gas-measuring device. The automated monitoring according to the present invention of switch-on and switch-off conditions also makes possible an especially high level of safety for the user in addition to an especially energy-efficient operation. Furthermore, this embodiment is advantageous due to the fact that mobile gas-measuring devices do not typically require manual operation, because a continuous monitoring of a working environment shall usually be ensured by such gas-measuring devices for the protection of the user from toxic gases. It is therefore possible for such a mobile gas-measuring device to avoid manual operating elements due to the automated switching between switched-on state and switched-off state in an especially advantageous manner and without further drawbacks.

The mobile measuring device is an optical measuring device or a sound detector in an embodiment that is an alternative to the above embodiment.

According to a second aspect of the present invention, a system for switching at least one mobile measuring device on and off automatically is proposed to accomplish the above-mentioned object. The system according to the present invention comprises at least one mobile measuring device according to the above-described variant concerning the reception of an identification signal for the detection of a position.

The system according to the present invention further comprises at least one signal transmitter, especially a number of signal transmitters located at spaced locations from one another, which are configured to output the identification signal. The detection unit of the mobile measuring device has the wireless module and the wireless module is configured to receive the identification signal if a distance between the mobile measuring device and one of the signal transmitters is shorter than a predefined identification distance.

The system according to the present invention ensures that the identification signal indicates a current location of the mobile measuring device, namely, an area predefined by the range of the signal transmitter. As a result, the system according to the present invention makes possible an especially reliable detection of the current position of the mobile measuring device as a function of the received identification signal.

In a preferred embodiment of the system according to the present invention, the system comprises both storage signal transmitters, which output an identification signal that indicates the presence of a storage state of the mobile measuring device, and use signal transmitters, which output an identification signal that indicates the presence of a use of the mobile measuring device. The storage signal transmitter is typically arranged in this embodiment in a storage area for the mobile measuring device, so that the mobile measuring device automatically detects on entry into this area that a switch-off condition is present, because no use is currently taking place and a change should therefore be carried out from the switched-on state into the switched-off state. The use signal transmitter is arranged, in turn, typically in an area of the safety-relevant application, so that the mobile measuring device automatically detects on entry into this area that a switch-on condition is present, because a use is currently taking place and a change from the switched-off state into the switched-on state should therefore be carried out.

The signal transmitters especially preferably have a range of less than 100 m, preferably less than 50 m, and especially less than 10 m. An accurate current position of the mobile measuring device can thus be inferred due to the reception of the identification signal assigned to the one signal transmitter.

According to a third aspect of the present invention, a process for switching at least one mobile measuring device on and off automatically is proposed to accomplish the above-mentioned object. The process according to the present invention has the following steps:

controlling a change between a switched-on state and a switched-off state of the mobile measuring device as a function of a received detection signal, automated monitoring in the switched-off state to determine whether a switch-on condition is present and outputting of the detection signal in the presence of the at least one switch-on condition, the detection signal indicating a change to be carried out into the switched-on state, wherein the switch-on condition comprises detection of a movement of the mobile measuring device, detection of a position of the mobile measuring device, detection of the ending of a charging process of the mobile measuring device or detection of a predefined current time, and automated monitoring in the switched-on state to determine whether at least two switch-off conditions are present and outputting of the detection signal in the presence of at least two switch-off conditions, the detection signal indicating a change to be carried out into the switched-off state, wherein the switch-off condition comprises detection of a continuous absence of movement, detection of a position of the mobile measuring device, detection of the start of a charging process of the mobile measuring device and/or detection of a predefined current time.

The process according to the present invention makes possible an especially reliable automated switching off because a change from the switched-on state into the switched-off state is only carried out in the presence of at least two switch-off conditions. In addition, the process makes possible an especially energy-saving operation of the mobile measuring device, because a switched-off state, in which energy is saved compared to the switched-on state, should be reached during phases during which the mobile measuring device is not being used.

In an especially preferred embodiment, the process further comprises the reception of a manual user input and a control between switched-on state and switched-off state depending on the manual user input. A switching over can advantageously be carried out in this embodiment between the switched-on state and the switched-off state manually directly after the safety-relevant application and/or directly before the safety-relevant application.

The present invention shall be explained now in more detail on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
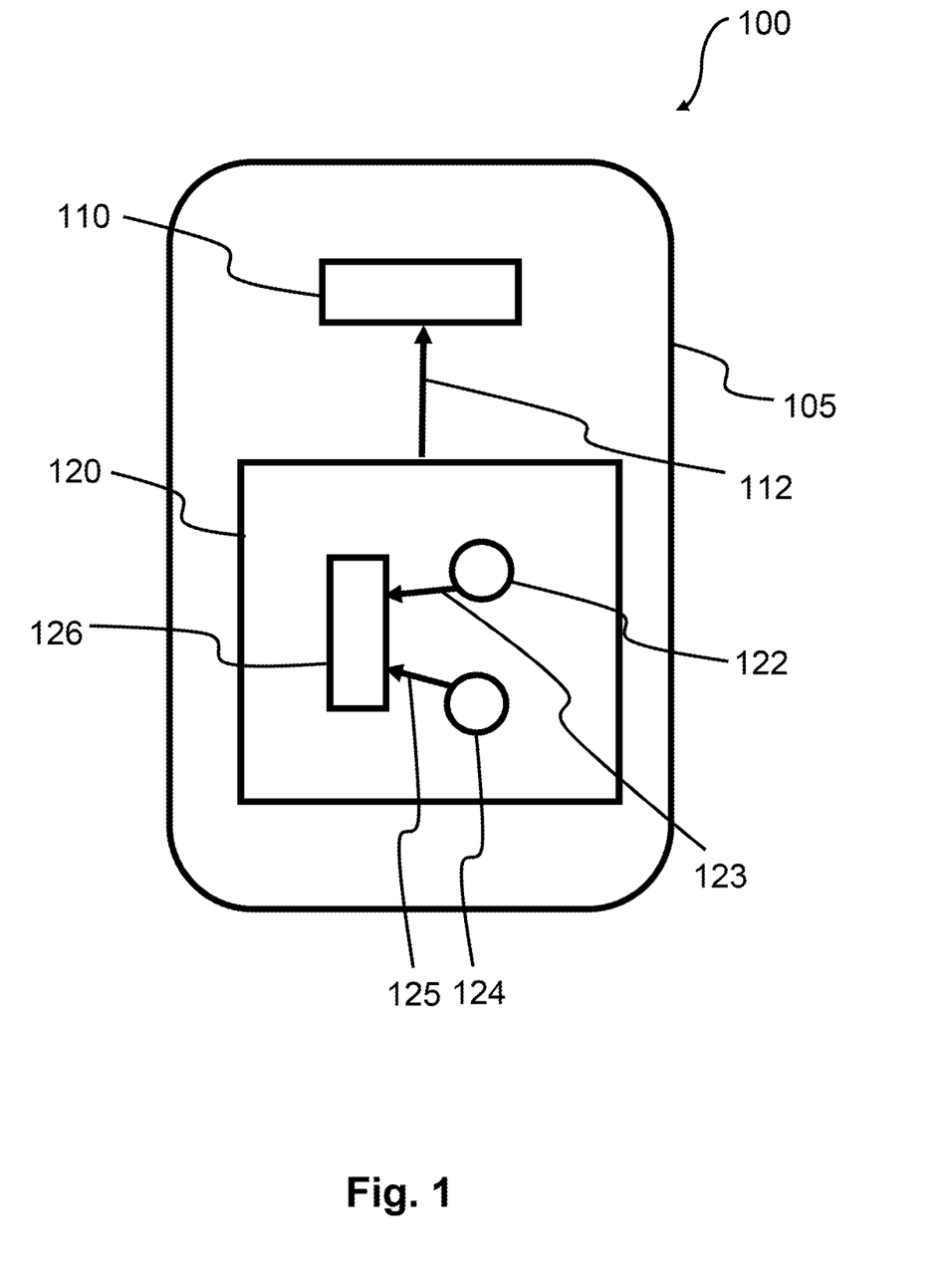
FIG. 1 is a schematic view of a first exemplary embodiment of a mobile measuring device according to the first aspect of the present invention.

Referring to the drawings, FIG. 1 shows a schematic view of a first exemplary embodiment of a mobile measuring device 100 according to the first aspect of the present invention.

The mobile measuring device 100 is configured for operation within the framework of a safety-relevant application. In the exemplary embodiment shown, the mobile measuring device 100 is a mobile gas-measuring device. The mobile measuring device 100 has a control unit 110 and a detection unit 120.

The control unit 110 is configured to control a change between the switched-on state and the switched-off state of the mobile measuring device 100 depending on a received detection signal 112. The detection signal 112 may indicate according to the present invention either a change of the operating state of the mobile measuring device 100 into the switched-on state, which change is to be carried out, or a change of the operating state into the switched-off state, which change is to be carried out, depending on the operating state that was present prior to the reception of the detection signal one and of the detection signal two. In the exemplary embodiment shown, the detection signal 112 indicates only a change of the current operating state into the respective other operating state. In one exemplary embodiment, not shown, the detection signal indicates detection information, which has additional information concerning the switch-on or switch-off conditions currently being met and/or concerning a type of the change in the operating state, which change is to be carried out, and/or concerning the operating state to be reached. Furthermore, the mobile measuring device has in one exemplary embodiment, not shown, a plurality of switched-on states and/or a plurality of switched-off states, which differ from each other, for example, in their energy consumption and/or especially in the detection devices that continue to be supplied with energy.

The detection unit 120 is configured to monitor in the switched-off state in an automated manner whether at least one switch-on condition is present and to output, in the presence of the at least one switch-on condition, the detection signal 112, which indicates change into the switched-on state, which change is to be carried out. The at least one switch-on condition comprises at least one element from the group of the following switch-on conditions: Detection of a movement of the mobile measuring device, detection of a position of the mobile measuring device, detection of the ending of a charging process of the mobile measuring device, and detection of a predefined current time.

In the exemplary embodiment shown, the detection unit 120 comprises a first detection device 122 and a second detection device 124. The first detection device 122 is a detection device for the detection of a movement and the second detection device 124 is a detection device for the detection of a time. The first detection device 122 is an acceleration sensor, which is configured to detect a movement of the mobile measuring device 100 and to output the presence of a switch-on condition via a first detection channel 123 to a processing unit 126 of the detection unit 120 during a detected movement. The second detection device 124 is a timer, which is configured to detect a predefined current time and to output the presence of a switch-on condition via a second detection channel 125 to the processing unit 126 of the detection unit 120 when this predefined current time is detected.

Thus, both of the two detection devices 122, 124 can detect each a separate switch-condition, and the detection of a single switch-on condition already leads to the detection signal 112 to be outputted for the change into the switched-on state, which change is to be carried out, to the control unit 110.

Furthermore, the detection unit 120 is configured to monitor in an automated manner in the switched-on state whether at least two switch-off conditions are present and to output the detection signal 112 that indicates a change into the switched-off state, which change is to be carried out, when at least two switch-off conditions are present. The at least two switch-off conditions comprise at least two elements from the following group of switch-off conditions: Detection of a continuous absence of movement, detection of a position of the mobile measuring device, detection of a start of a charging process of the mobile measuring device, and detection of a predefined current time.

The detection of the continuous absence of movement is carried out by the first detection device 122 and the detection of the predefined current time is carried out by the second detection device 124 in the exemplary embodiment shown. In the presence of a respective switch-off condition, information concerning the presence of a respective switch-off condition is outputted to the processing unit 126 of the detection unit 120 via the respective detection channel 123, 125. The detection unit 120 triggers a change of the operating state of the mobile measuring device 100 by the control unit 110 via the detection signal 112 only in the presence of both switch-off conditions. An accidental switching off is avoided hereby. It is ensured due to the fact that the two switch-off conditions are detected by two separate detection devices 122, 124 that a malfunction of one detection device cannot lead to an incorrect switching off of the mobile measuring device 100 during a safety-relevant application.

In one exemplary embodiment, not shown, a corresponding detection signal is outputted out of a switched-on state only when at least two switch-on conditions were detected by the detection devices of the detection unit.

In one exemplary embodiment, not shown, the detection device for detecting a movement is a brightness sensor, a vibration sensor, a temperature sensor, a tilt switch and/or an optical sensor.

In the exemplary embodiment shown, the mobile measuring device 100 has no manual operating elements. It can be ensured hereby in an especially reliable manner that no manual operating error, e.g., an accidental switching on or switching off, will take place. Furthermore, the mobile measuring device 100, i.e., the gas-measuring device in this exemplary embodiment, has an output element (not shown), especially an LED diode, which indicates the presence of an alarm state. Furthermore, the output element can indicate the current operating state of the mobile measuring device 100, for example, by a light in a predefined color in the case of the switched-on state and by an absence of light in the switched-off state.

Due to the fact no manual operating elements exist, the mobile measuring device 100 can be manufactured and mounted in an especially simple and cost-effective manner. Furthermore, a robust housing 105, which is also suitable for operation in the area subject to explosion hazard, can be manufactured as a result in an especially simple manner.

Figure 2:
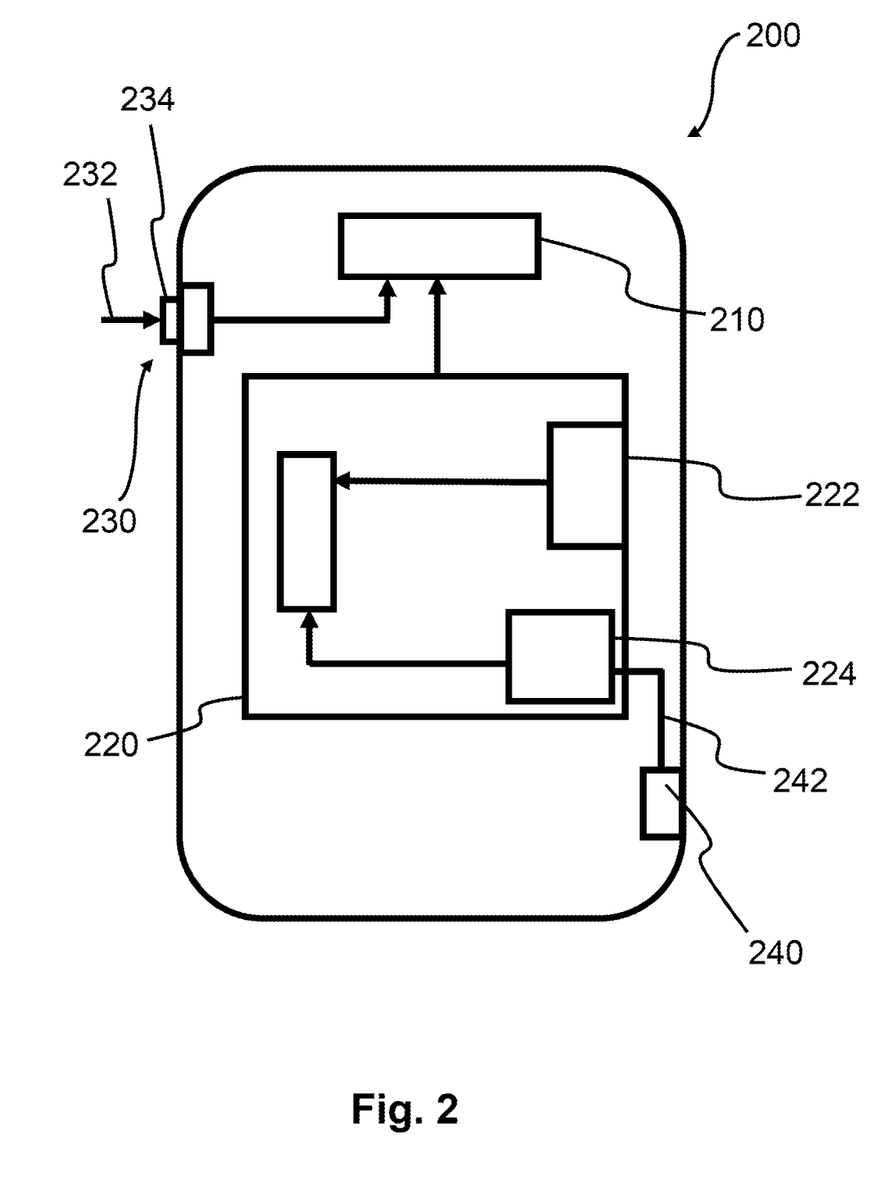
FIG. 2 is a schematic view of a second exemplary embodiment of the mobile measuring device according to the first aspect of the present invention.

FIG. 2 shows a schematic view of a second exemplary embodiment of the mobile measuring device 200 according to the first aspect of the present invention.

The mobile measuring device 200 differs from the mobile measuring device 100 shown in FIG. 1 in that it has a user interface 230, which is configured to receive a manual user input 232. The user interface 230 is a button 234 in the exemplary embodiment shown. The control unit 210 is further configured to control the change between the switched-on state and the switched-off state as a function of the manual user input 232.

In the preferred exemplary embodiment shown, the mobile measuring device 200 can be switched on via the user interface 230 by pressing the button 234 and it can thus be brought from the switched-off state into the switched-on state. The change into the switched-off state via the user interface 230 is not possible. It is ensured hereby that an accidental switching off by the user of the mobile measuring device 200 will not take place. In one exemplary embodiment, not shown, a change into the switched-off state of the mobile measuring device can, furthermore, be carried out via the user interface. In another exemplary embodiment, not shown, the user interface is an adjusting wheel or a touch sensor.

Further, the mobile measuring device 200 differs from the measuring device 100 shown in FIG. 1 in that the detection unit 220 has other detection devices 222, 224. The first detection device 222 is a detection device for the detection of a position, namely, a GPS sensor. In one exemplary embodiment, not shown, the detection device for detecting a position is an induction module. The GPS sensor is configured to analyze a current position of the mobile measuring device 200 and to indicate the presence of a switch-on or switch-off condition depending on whether the current position is within a predefined storage area. If the mobile measuring device 200 changes over from a position outside the storage area into a position within the storage area, the presence of a switch-off condition is indicated, because storage of the mobile measuring device 200 is expected to begin. If the storage area has been left by the mobile measuring device 200, the presence of a switch-on condition is indicated, because the storage of the mobile measuring device 200 is expected to have ended.

Furthermore, unlike in the mobile measuring device 100 from FIG. 1, the second detection device 224 is a detection device for the detection of a beginning or ending of a charging process of the mobile measuring device 200, namely, a detector, which detects a change within an energy supply by an induction module 240. An electrical connection 242 exists for this purpose between the induction module 240 and the second detection device 224. The second detection device 224 detects here a change in the energy supply such that separation of the mobile measuring device from an external inductive charging station is detected, which is indicative of an imminent use of the mobile measuring device 200, so that such a change is indicated as the presence of a switch-on condition. If the beginning of an inductive charging process is detected by the second detection device 224, the presence of a switch-off condition is indicated, because the mobile measuring device 200 is not typically being charged during use.

In one exemplary embodiment, not shown, the detection unit of the mobile measuring device comprises more than two detection devices.

Figure 3:
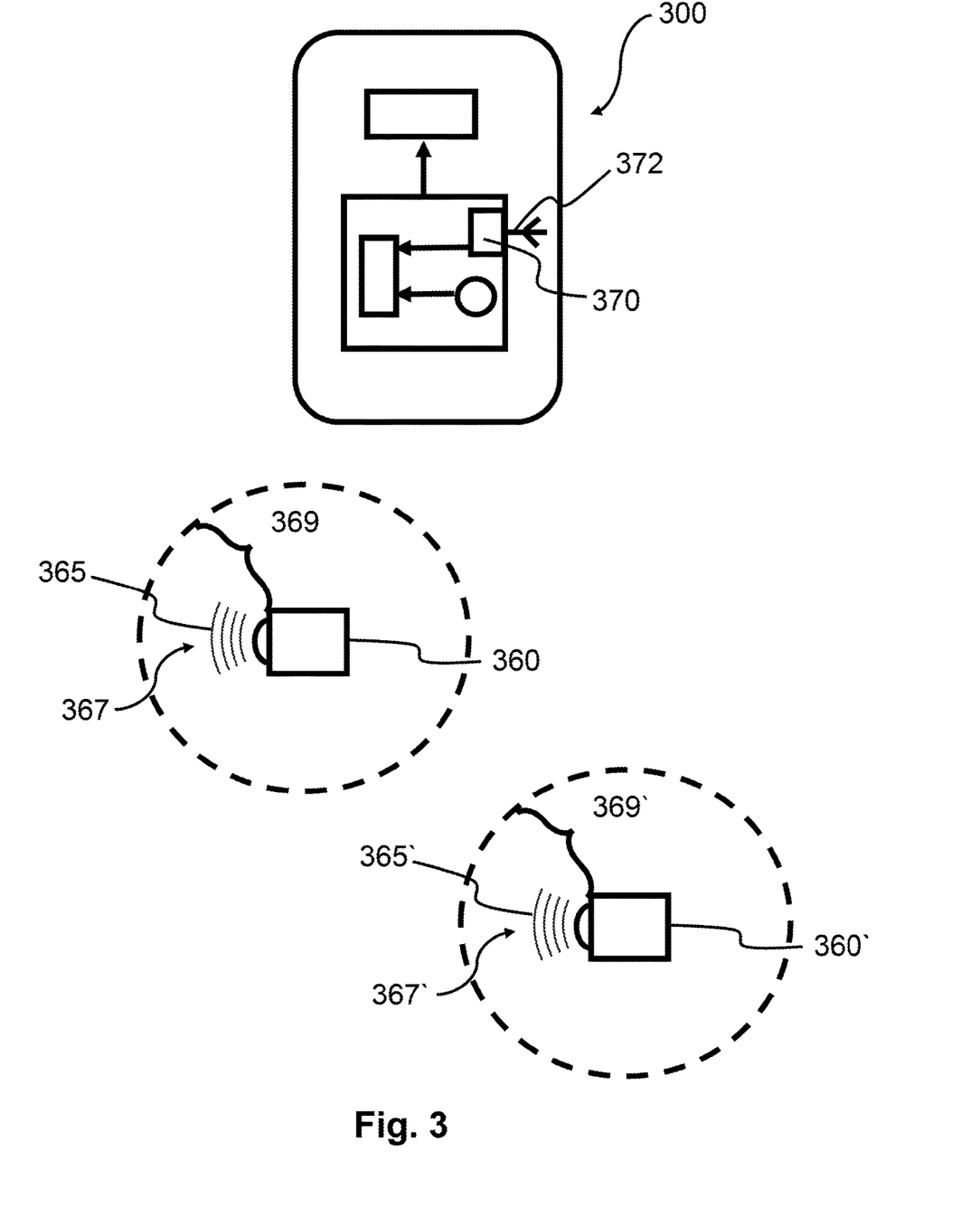
FIG. 3 is a schematic view of an exemplary embodiment of a system according to the second aspect of the present invention.

FIG. 3 shows a schematic view of an exemplary embodiment of a system 350 according to the second aspect of the present invention.

The system 350 for the automatic switching on and switching off of at least one mobile measuring device 300 comprises at least one mobile measuring device 300 and a number of signal transmitters 360, 360' located at spaced locations from one another.

According to the second aspect of the present invention, the mobile measuring device 300 comprises a detection unit with at least one detection device, which comprises a wireless module 370 and is suitable for the detection of the position of the mobile measuring device 300. The wireless module 370 comprises here an antenna 372 for receiving a radio signal.

The number of signal transmitters 360, 360' located at spaced locations from one another comprises two signal transmitters 360, 360' in the exemplary embodiment shown.

These two signal transmitters 360, 360' are configured to output a respective identification signal 365, 365' each, which indicates a respective piece of identification information 367, 367'.

The wireless module 370 with the antenna 372 is configured to receive the respective identification signal 365, 365' in case of a sufficiently short distance from the respective signal transmitter 360, 360' and to indicate the change between switched-on state and switched-off state, which change is to be carried out, especially the presence of a corresponding switch-on or switch-off condition, depending on the indicated identification information 367, 367'. The current position of the mobile measuring device 300 can be inferred now on the basis of the identification signal. If, for example, the identification signal of a signal transmitter located within a storage location is received, an expected end of a use is assumed, so that a switch-off condition is present. If, by contrast, the identification signal of a signal transmitter located within the location of use is received, the presence of a switch-on condition is indicated, because current use is assumed.

In one exemplary embodiment, not shown, the system according to the present invention comprises only one signal transmitter. This signal transmitter is positioned, for example, at a location of use of the mobile measuring device.

In the exemplary embodiment shown, a respective identification distance 369, 369', up to which the respective identification signal 365, 365' can be transmitted with sufficient signal strength, so that it can be reliably received by the wireless module 370 such that the identification information 367, 367' can be read out, is assigned to each signal transmitter 360, 360'.

Figure 4:
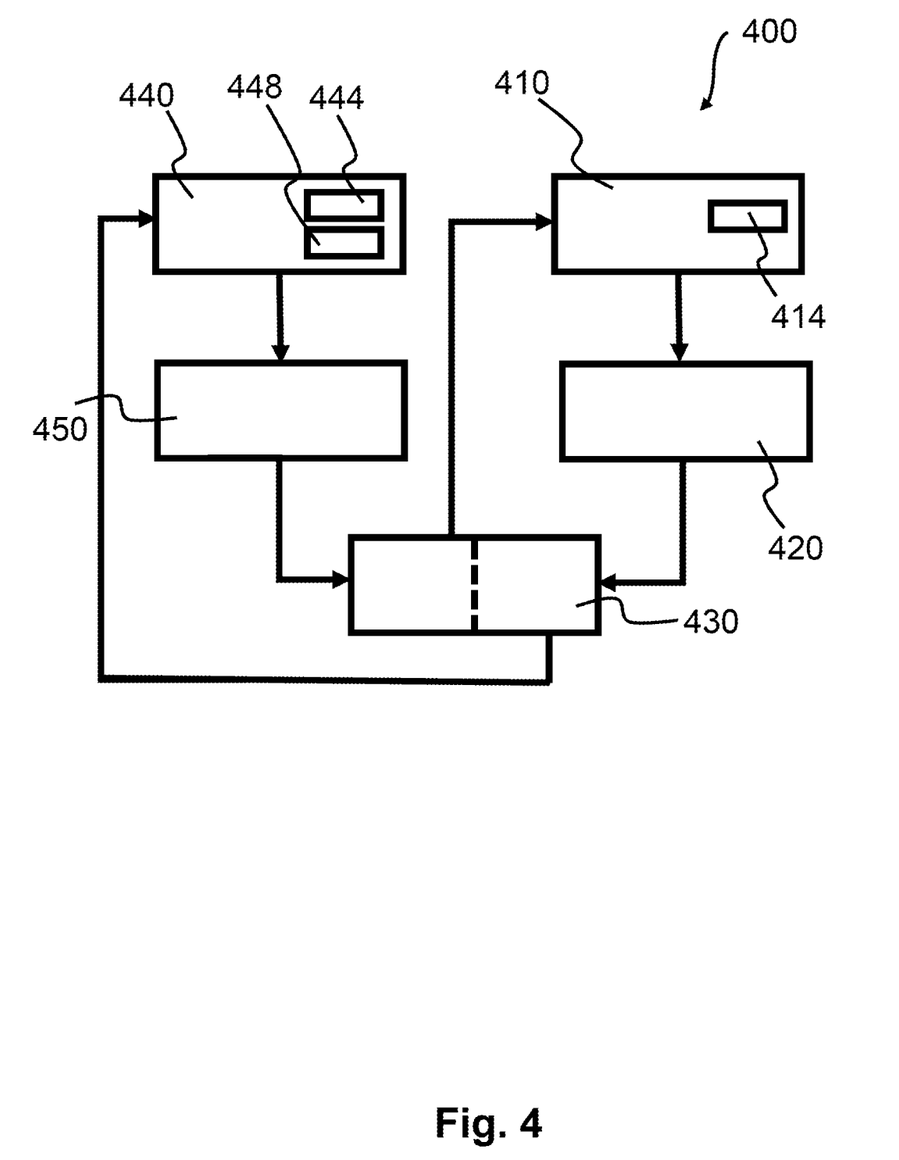
FIG. 4 is a flow chart of an exemplary embodiment of a process according to the third aspect of the present invention.

FIG. 4 shows a flow chart of an exemplary embodiment of a process 400 according to the third aspect of the present invention.

The process 400 according to the present invention for the automatic switching on and switching off of at least one mobile measuring device has the process steps explained below.

A first step 410 comprises an automated monitoring in the switched-off state to determine whether a switch-on condition 414 is present, wherein the switch-on condition 414 comprises detection of a movement of the mobile measuring device, detection of a position of the mobile measuring device, detection of the ending of a charging process of the mobile measuring device and/or detection of a predefined current time.

A next step 420 comprises in the presence of the at least one switch-on condition 414 the outputting of a detection signal, which indicates a change into the switched-on state, which change is to be carried out.

A next step 430 comprises the control of a change between a switched-on state and a switched-off state of the mobile measuring device depending on a received detection signal.

A next step 440, which may also be an alternative first step of the process according to the present invention depending on a start state of the mobile measuring device, comprises an automated monitoring in the switched-on state to determine whether at least two switch-off conditions 444, 448 are present, the switch-off conditions 444, 448 comprising detection of a continuous absence of movement, detection of a position of the mobile measuring device, detection of a start of a charging process of the mobile measuring device and/or detection of a predefined current time.

Another step 450 comprises in the presence of at least two switch-off conditions 444, 448 the outputting of a detection signal, which indicates a change into the switched-off state, which change is to be carried out.

Step 430 is, in turn, carried out after step 450. Whether the process begins with step 410 or with step 440 depends on whether the mobile measuring device is at the beginning of the process in the switched-on state or in the switched-off state. Step 410 is followed in case of the detection of the switch-on condition by the steps 420 and 430. Step 440 is followed in case of the detection of the at least two switch-off conditions by the steps 450 and 430. Step 430 is followed, depending on the state of the mobile measuring device prior to the change to be carried out, by step 410 or step 440.

While specific embodiments of the invention have been shown and described in detail to illustrate the application of the principles of the invention, it will be understood that the invention may be embodied otherwise without departing from such principles.

LIST OF REFERENCE NUMBERS 100, 200, 300 Mobile measuring device
105 Housing
110, 210 Control unit
112 Detection signal
120, 220 Detection unit
122, 222 First detection device
123 First detection channel
124, 224 Second detection device
125 Second detection channel
126 Processing unit of the detection device
230 User interface
232 Manual user input
234 Button
240 Induction module
242 Electrical connection
350 System
360, 360' Signal transmitter
365, 365' Identification signal
367, 367' Identification information
369, 369' Identification distance
370 Wireless module
372 Antenna
400 Process
410, 420, 430, 440, 450 Process steps
414 Switch-on condition
444, 448 Switch-off condition

What is claimed is:

1. A mobile measuring device for a safety-relevant application, the mobile measuring device comprising:
a control unit configured to control a change between a switched-on state and a switched-off state of the mobile measuring device, depending on a received detection signal which indicates a change between the switched-on state and the switched-off state, the mobile measuring device being configured to monitor an environment for a toxic gas in the switched-on state; and
a detection unit, which is configured, in the switched-off state, to automatedly monitor whether at least one switch-on condition is present and to output the detection signal in the presence of the at least one switch-on condition, wherein the detection signal indicates a change into the switched-on state, which change is to be carried out, wherein the switch-on condition comprises detection of at least one of a movement of the mobile measuring device, detection of a position of the mobile measuring device and detection of a predefined current time, and wherein the detection unit is further configured, in the switched-on state, to automatedly monitor whether at least a first switch-off condition and a second switch-off condition are present and to output the detection signal in the presence of at least the first switch-off condition and the second switch-off condition, wherein the detection signal indicates a change into the switched-off state, which change is to be carried out, wherein the first switch-off condition is one of detection of a continuous absence of movement of the mobile measuring device, detection of a position of the mobile measuring device, detection of a beginning of a charging process of the mobile measuring device and detection of a predefined current time, wherein the second switch-off condition is another one of the detection of the continuous absence of movement of the mobile measuring device, the detection of the position of the mobile measuring device, the detection of the beginning of the charging process of the mobile measuring device and the detection of the predefined current time, and wherein the detection unit further comprises at least two detection devices, which are configured to each carry out a detection corresponding to the at least one switch-on condition and to at least the first switch-off condition and the second switch-off condition, wherein the mobile measuring device is a mobile gas-measuring device.

2. A mobile measuring device in accordance with claim 1, wherein the detection unit is configured to monitor whether at least two switch-on conditions are present and to output the corresponding detection signal in the presence of the at least two switch-on conditions.

3. A mobile measuring device in accordance with claim 1, further comprising a user interface configured to receive a manual user input, wherein the control unit is further configured to control the change between the switched-on state and the switched-off state depending on the manual user input.

4. A mobile measuring device in accordance with claim 1, wherein:
one of the at least two detection devices of the detection unit comprises a movement detection device configured to detect a movement; and
the movement detection device comprises an acceleration sensor, a brightness sensor, a vibration sensor, a temperature sensor, a tilt switch and/or an optical sensor.

5. A mobile measuring device in accordance with claim 1, wherein:
one of the at least two detection devices of the detection unit comprises a position detection device configured to detect a position; and
the position detection device comprises a GPS sensor, a wireless module, an optical sensor, a magnetic sensor and/or an induction module.

6. A mobile measuring device in accordance with claim 1, wherein:
one of the at least two detection devices of the detection unit comprises a time detection device configured to detect a time; and
the time detection device comprises a timer.

7. A mobile measuring device in accordance with claim 1, wherein:
one of the at least two detection devices of the detection unit comprises a charging process detection device configured to detect a beginning or an ending of a charging process; and
the charging process detection device is configured to detect at least one of a change in an electric power fed to the mobile measuring device and a severing or connection of an electrical or inductive contact via a corresponding connection.

8. A mobile measuring device in accordance with claim 5, wherein the wireless module receives an identification signal and is configured to indicate the change between switched-on state and switched-off state depending on identification information indicated by the received identification signal.

9. A mobile device automatic switching on and switching off system comprising:
a mobile measuring device comprising a control unit configured to control a change between a switched-on state and a switched-off state of the mobile measuring device, depending on a received detection signal which indicates a change between the switched-on state and the switched-off state, and a detection unit, which is configured, in the switched-off state, to automatedly monitor whether at least one switch-on condition is present and to output the detection signal in the presence of the at least one switch-on condition, wherein the detection signal indicates a change into the switched-on state, which change is to be carried out, wherein the switch-on condition comprises at least one of detection of a movement of the mobile measuring device, detection of a position of the mobile measuring device and detection of a predefined current time, and wherein the detection unit is further configured, in the switched-on state, to automatedly monitor whether at least a first switch-off condition and a second switch-off condition are present and to output the detection signal in the presence of at least the first switch-off condition and the second switch-off condition, wherein the detection signal indicates a change into the switched-off state, which change is to be carried out, wherein the first switch-off condition is one of detection of a continuous absence of movement of the mobile measuring device, detection of a position of the mobile measuring device, detection of a beginning of a charging process of the mobile measuring device and detection of a predefined current time, wherein the second switch-off condition is another one of the detection of the continuous absence of movement of the mobile measuring device, the detection of the position of the mobile measuring device, the detection of the beginning of the charging process of the mobile measuring device and detection of the predefined current time and wherein the detection unit further comprises at least two detection devices, which are configured to each carry out a detection corresponding to the at least one switch-on condition and to the at least two switch-off conditions, wherein one of the at least two detection devices of the detection unit comprises a position detection device configured to detect a position, the position detection device comprises at least one of a GPS sensor, a wireless module, an optical sensor, a magnetic sensor and an induction module, and the wireless module receives an identification signal and is configured to indicate the change between switched-on state and switched-off state depending on identification information indicated by the received identification signal, the mobile measuring device being configured to monitor an environment for a toxic gas in the switched-on state; and a plurality of signal transmitters located at spaced locations from one another, each of the plurality of signal transmitters being configured to output the identification signal, and wherein the wireless module is configured to receive the identification signal if a distance between the mobile measuring device and one of the plurality of signal transmitters is shorter than a predefined identification distance.

10. A process for an automatic switching on and switching off of at least one mobile measuring device, the process comprising the steps of:

controlling a change between a switched-on state and a switched-off state of the mobile measuring device depending on a received detection signal which indicates a change between the switched-on state and the switched-off state, the mobile measuring device being configured to monitor an environment for a toxic gas in the switched-on state, wherein the mobile measuring device is a mobile gas-measuring device;

automatedly monitoring, in the switched-off state, to determine whether at least one switch-on condition is present and outputting of the detection signal in the presence of the at least one switch-on condition, wherein the detection signal indicates a change into the switched-on state, which change is to be carried out, wherein the switch-on condition comprises detection of a movement of the mobile measuring device, detection of a position of the mobile measuring device, detection of the ending of a charging process of the mobile measuring device or detection of a predefined current time; and automatedly monitoring, in the switched-on state, to determine whether at least two switch-off conditions are present, and outputting of the detection signal in the presence of at least a first switch-off condition and a second switch-off condition, wherein the detection signal indicates a change into the switched-off state, which change is to be carried out, wherein the first switch-off condition is one of detection of a continuous absence of movement of the mobile measuring device, detection of a position of the mobile measuring device, detection of the beginning of a charging process of the mobile measuring device and detection of a predefined current time, wherein the second switch-off condition is another one of the detection of the continuous absence of movement of the mobile measuring device, the detection of the position of the mobile measuring device, detection of the beginning of the charging process of the mobile measuring device and detection of the predefined current time.

11. A process in accordance with claim 10, wherein the mobile measuring device is configured to not monitor the environment for the toxic gas in the switched-off state.

12. A mobile device automatic switching on and switching off system in accordance with claim 9, wherein the mobile measuring device is configured to not monitor the environment for the toxic gas in the switched-off state.

13. A mobile measuring device in accordance with claim 1, wherein the mobile measuring device is configured to not monitor the environment for the toxic gas in the switched-off state.

* * * * *